United States Patent [19]
Biel

[11] Patent Number: 6,083,487
[45] Date of Patent: Jul. 4, 2000

[54] METHYLENE BLUE AND TOLUIDENE BLUE MEDIATED FLUORESCENCE DIAGNOSIS OF CANCER

[75] Inventor: Merrill A. Biel, Mendota Heights, Minn.

[73] Assignee: Advanced Photodynamic Technologies, Inc., Mendota Heights, Minn.

[21] Appl. No.: 09/139,481

[22] Filed: Aug. 25, 1998

Related U.S. Application Data

[60] Provisional application No. 60/057,356, Aug. 25, 1997.
[51] Int. Cl.[7] ............................. A61B 10/00; G01N 21/76
[52] U.S. Cl. ............................. 424/9.6; 424/9.7; 424/9.8; 436/172; 436/800
[58] Field of Search .................................... 424/9.6, 9.61, 424/9.7, 9.8, 9.1; 600/317; 435/968; 436/172, 800

[56] References Cited

U.S. PATENT DOCUMENTS 5,372,801  12/1994  Malmros et al. ........................ 424/9.7

OTHER PUBLICATIONS

Gill, W.B. et al., Selective Surface Staining of Bladder Tumors by Intravesical Methylene Blue with Enhanced Endoscopic Identification, Cancer, 53, 2724–2727, 1984.

Peng, Q. et al., Biodistribution of a methylene blue derivative in tumor and normal tissues of rats, Jour. Photochem. Photobiol, B: Biol., 20, 63–71, 1993.

*Primary Examiner*—Jose' G. Dees
*Assistant Examiner*—Michael G. Hartley
*Attorney, Agent, or Firm*—Larkin, Hoffman, Daly & Lindgren, Ltd.

[57] ABSTRACT

A method for differentiating between normal tissue and tumor tissue within a tissue field. The method includes the application of a photosensitizer solution to the tissue field and the subsequent illumination and measurement of fluorescent intensity across the tissue field. The measurement of relative fluorescent intensity across the tissue field provides information relating to the existence or nonexistence of tumor tissue. Solution concentrations of methylene blue and or toluidene blue are utilized to provide the greatest differentiability between normal tissue and tumor tissue within the tissue field.

7 Claims, 4 Drawing Sheets

METHYLENE BLUE AND TOLUIDENE BLUE MEDIATED FLUORESCENCE DIAGNOSIS OF CANCER

CROSS REFERENCE TO RELATED APPLICATIONS

This application claims the benefit of priority pursuant to 35 USC §119(e)(1) from the provisional patent application filed pursuant to 35 USC §111(b): as Ser. No. 60/057,356 on Aug. 25, 1997.

BACKGROUND OF THE INVENTION

1. Field of the Invention

Photodynamic therapy (PDT) is a medical technology which uses light energy in combination with photosensitizing agents to treat or detect pathologies of living tissue, including cancer and microbiological pathogens. Once presensitized by the photosensitizing agent, the cancerous or abnormal cells can be detected by irradiation with light of an appropriate wavelength or waveband corresponding to an absorbing wavelength of the agent, with minimal damage to normal tissue. This procedure has been clinically used to detect a variety of cancers and tumors. Because PDT may be selective in detecting abnormal cells that have absorbed more of the agent, it can successfully be used to detect malignant tissue with less effect on surrounding benign tissue.

2. Brief Discussion of the Prior Art

Photodynamics provides a diagnosis tool that involves the use of a photosensitizing agent and a specific wavelength of light to detect tissue abnormalities. A photodynamic detection system consists of principal components: a photosensitizing agent, a light source (typically a laser), a light delivery means (typically optical fiber based); and a detection device. Two principal challenges for this emerging field of medicine are the development and validation of photosensitizer agents, and the development of reliable wavelength specific (laser) light sources at appropriate and convenient energy levels.

Photodynamic medical diagnosis entails the use of a photosensitizing agent that is relatively selectively concentrated in cancer cells or microbiological pathogen sites. Depending on the type of photosensitizer, it may be injected intravenously, ingested orally, or applied topically. After application of the photosensitizer, it is selectively retained by diseased tissue so that after a period of time, determined by the kinetics of the compound's distribution, there is more photosensitizer in the diseased tissue than in the normal tissue. The photosensitizer is then activated with a specific wavelength of light matching the absorption characteristics of the specific photosensitizer, typically using a laser.

SUMMARY OF THE INVENTION

The present invention is method for selective tumor fluorescence identification using methylene blue and toluidene blue. A solution of methylene blue or toluidene blue may be administered to a tissue site and later illuminated with an appropriate laser having a wavelength causing fluorescence of the photosensitized tissue. Administration of the methylene blue or toluidene blue may be a topical application. The present invention may be used in conjunction with or in relation to inventions disclosed in the following applications, filed on the same date concurrently herewith, Aug. 25, 1998.

U.S. Patent Applications: M. Biel, Inventor:
  Method of Enhancing Photodynamic Therapy by Administering an Immunologic Adjuvant, Ser. No. 09/139,861.
  Dye Treatment Solution and Photodynamic Therapy and Method of Using Same, Ser. No. 09/139,866.
  Spatial Orientation Grid and Light Sources and Method of Using Same for Medical Diagnosis and Photodynamic Therapy, Ser. No. 09/139,862.
  Rectangular Laser Irradiation Field Producing Apparatus for Medical Treatment, Ser. No. 09/139,480.

PCT Application: M. Biel, Inventor
  Treatment Device for Topical Photodynamic Therapy and Method of Making Same, PCT/US98/17589.

All documents within these applications are herein incorporated by reference in their entireties for all purposes.

DETAILED DESCRIPTION OF THE PREFERRED EMBODIMENTS

A preferred method of use according to the present invention includes the topical application at a tissue site of a saline solution having a methylene blue concentration of between approximately 0.010–0.020%. After a brief activation time of up to 10 minutes, the tissue site may be washed with a saline or acetic acid solution. The tissue field is subsequently illuminated by a light source, preferably a laser providing light energy at approximately 660 nm. Methylene blue fluoresces at 685 nm and such tissue field fluorescence may be detected by a light detector, such as a photomultiplier or similar instrument. The detection of a tumor is made by the comparison of the relative fluorescence between the tumor site and the surrounding normal tissue.

Figure 1:
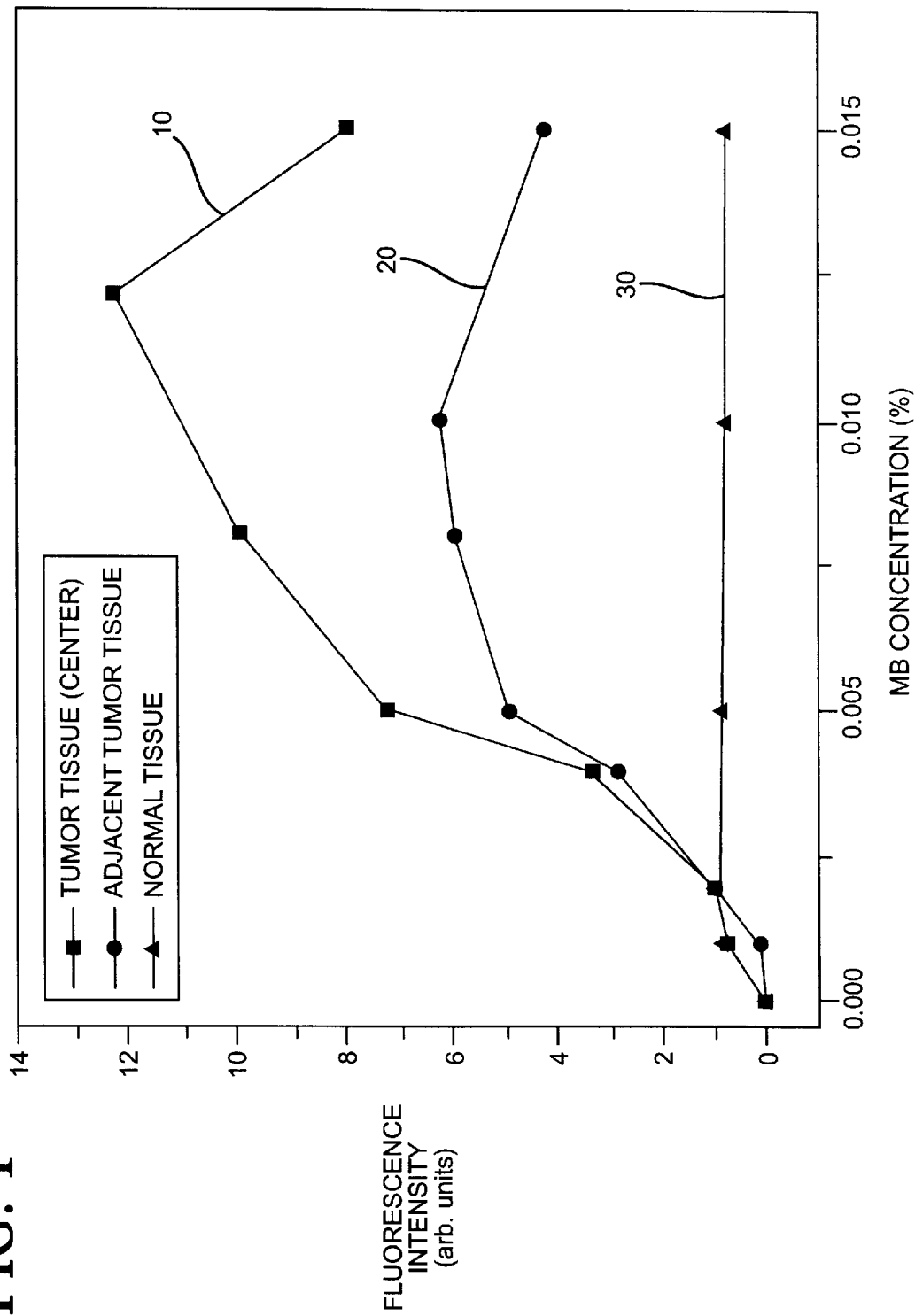
Figure 2:
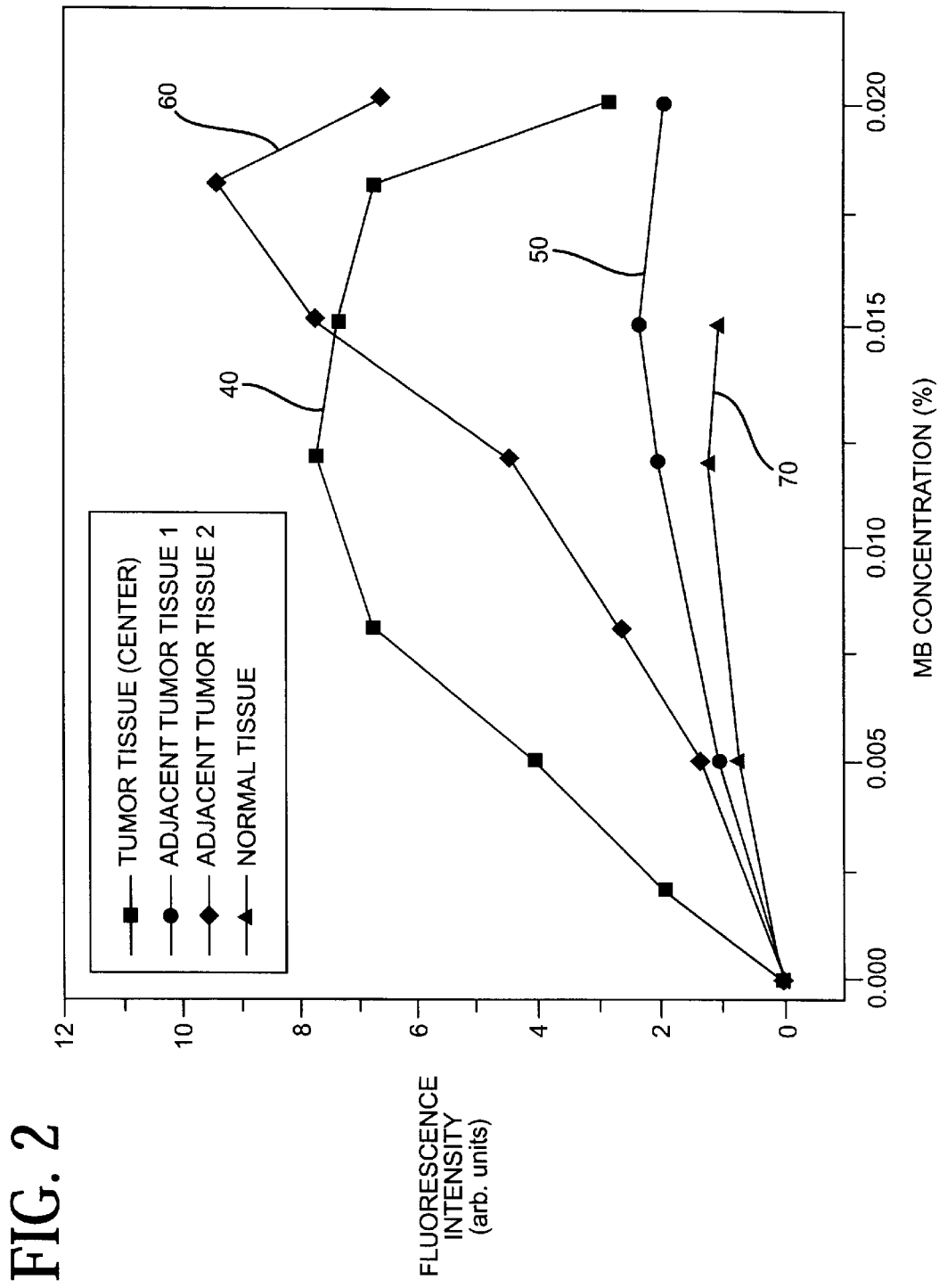

FIGS. 1 and 2 illustrate relative fluorescence intensity as a function of methylene blue concentration. Included in FIG. 1 are data for tumor tissue 10, adjacent tumor tissue 20, and normal tissue 30. FIG. 1 Illustrates a smaller relative difference between tumor tissue 10 and normal tissue 30 at lower methylene blue concentrations (less than 0.005%) and again at higher concentrations (greater than 0.015%). The largest relative difference (and hence providing the greatest fluorescent differentiation between the two tissues 10 30) between tumor tissue 10 and normal tissue 30 occurs between 0.0075% and 0.02%. Included in FIG. 2 are data for tumor tissue (center) 40, adjacent tumor tissue 50, adjacent tumor tissue 60, and normal tissue 70. FIG. 2 illustrates that at methylene blue concentrations greater than 0.020%, the relative differences between the tissues 40 50 60 70 decreases (tumor fluorescence delectability decreases).

Another method of use according to the present invention includes the topical application at a tissue site of a saline solution having a toluidene blue concentration of between approximately 0.0005–0.020%. After a brief activation time of up to 10 minutes, the tissue site may be washed with a saline or acetic acid solution. The tissue field is subsequently illuminated by a light source, preferably a laser providing light energy at approximately 630 nm. Toluidene blue fluoresces at 652 nm and such tissue fluorescence may be detected by a light detector, such as a photomultiplier or similar instrument. The detection of a tumor is made by the comparison of the relative fluorescence between the tumor site and the surrounding normal tissue.

Figure 3:
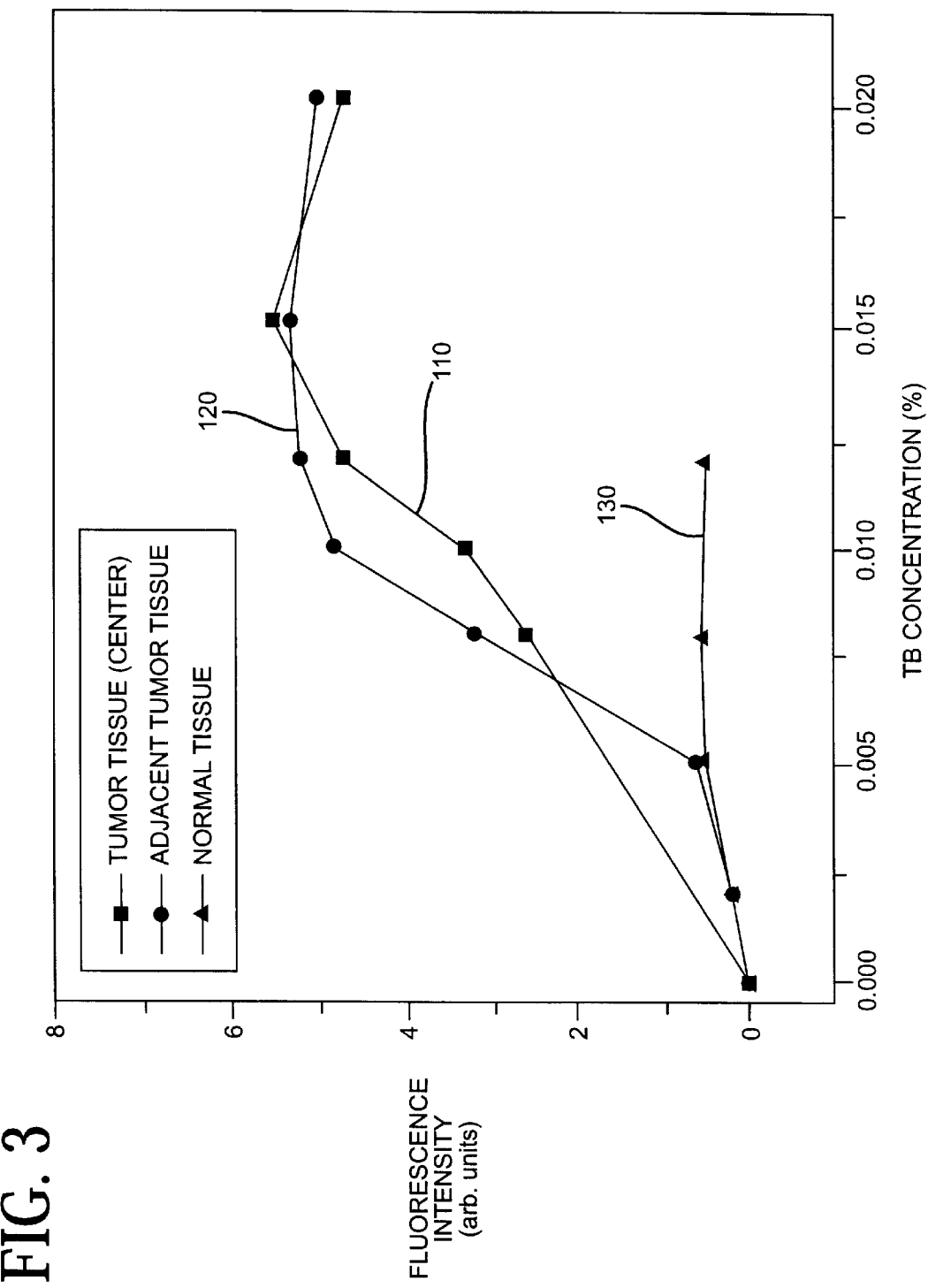
Figure 4:
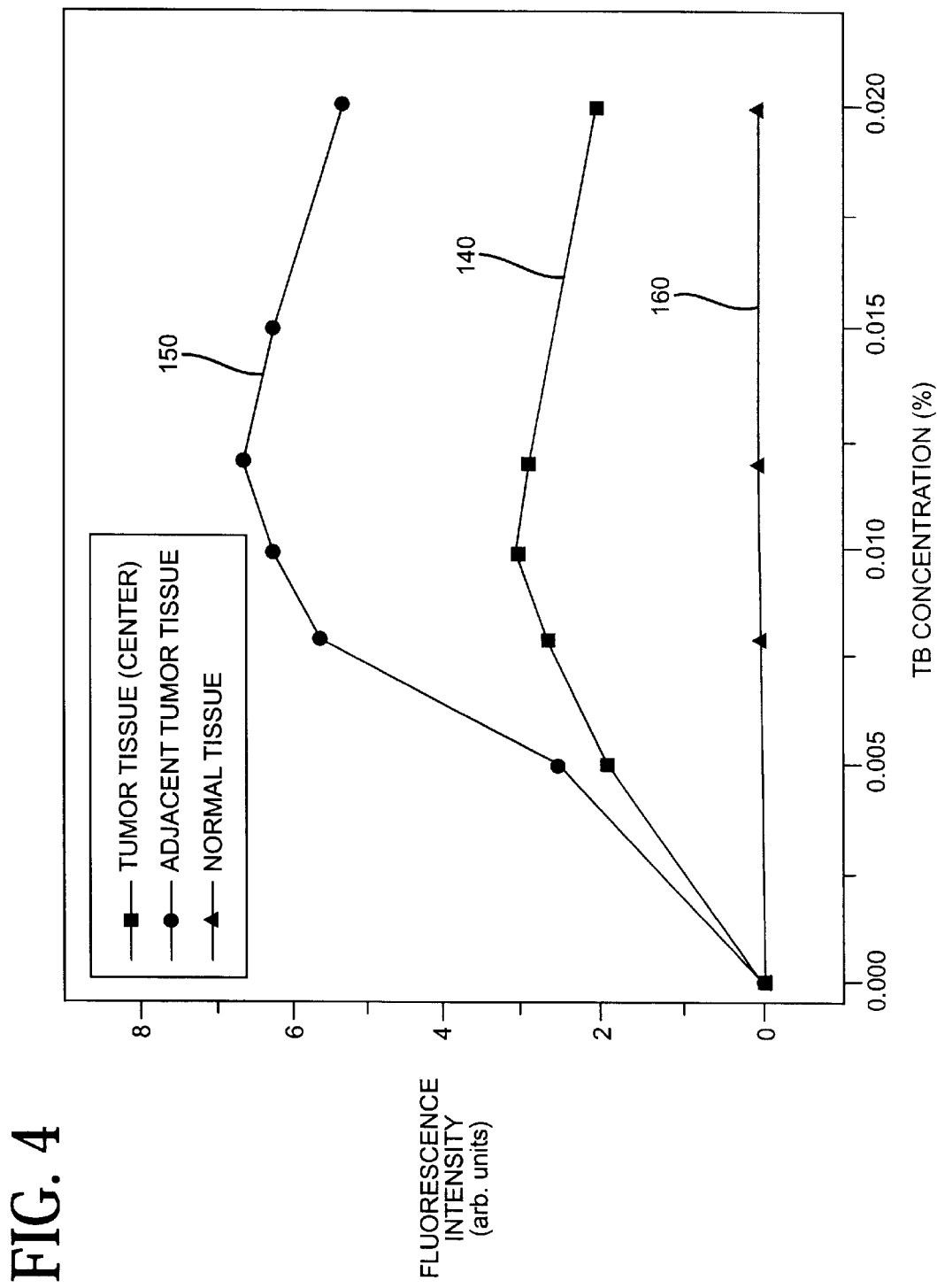

FIGS. 3 and 4 illustrate relative fluorescence intensity as a function of toluidene blue concentration. Included in FIG. 3 are data for tumor tissue 110, adjacent tumor tissue 120, and normal tissue 130. FIG. 3 Illustrates a smaller relative difference between tumor tissue 110 and normal tissue 130 at lower toluidene blue concentrations (less than 0.005%). Included in FIG. 4 are data for tumor tissue 140, adjacent tumor tissue 150, and normal tissue 160. FIG. 4 illustrates that at higher toluidene blue concentrations, the relative fluorescence intensity difference between the tissues 140 150 160 decreases (tumor fluorescence delectability decreases). The largest relative difference (and hence providing the greatest fluorescent differentiation between the tissues ) between tumor tissue 110 and normal tissue 130 occurs between 0.005% and 0.02% toluidene blue concentration.

While the preferred embodiments of the above method have been described in detail, it is understood that various changes and adaptations may be made without departing from the spirit and scope of the appended claims.

What is claimed is:

1. A method of detecting tumor sites within a tissue field having normal tissue, said method comprising the following steps:

identifying a tissue site for treatment;

administering a photosensitizing solution having a concentration of methylene blue between 0.0075% and 0.02% to said tissue site;

allowing said tissue site to respond to the photosensitizing solution during a period of time;

illuminating said tissue site with light energy at approximately 660 nm to promote a photodynamic response, said photodynamic response including a difference in fluorescence intensity between the tumor site and the normal tissue;

detecting said difference in fluorescence intensity between the tumor site and the normal tissue; and differentiating between the tumor site and the normal tissue based upon the difference in fluorescence intensity between the tumor site and the normal tissue.

2. The method of claim 1 wherein the photosensitizing solution is administered topically.

3. The method of claim 1 wherein the period of time is up to ten minutes.

4. A method of detecting tumor sites within a tissue field having normal tissue, said method comprising the following steps:

identifying a tissue site for treatment;

administering a photosensitizing solution having a concentration of toluidene blue between 0.005% and 0.02% to said tissue site;

allowing said tissue site to respond to the photosensitizing solution during a period of time;

illuminating said tissue site with light energy at approximately 630 nm to promote a photodynamic response, said photodynamic response including a difference in fluorescence intensity between the tumor site and the normal tissue;

detecting said difference in fluorescence intensity between the tumor site and the normal tissue; and differentiating between the tumor site and the normal tissue based upon the difference in fluorescence intensity between the tumor site and the normal tissue.

5. The method of claim 4 wherein the photosensitizing solution is administered topically.

6. The method of claim 4 wherein the period of time is up to ten minutes.

7. The method of claim 4 wherein the tumor site fluoresces with a higher relative fluorescent intensity than the normal tissue.

* * * * *